United States Patent [19]

Matsuda et al.

[11] Patent Number: 6,033,862

[45] Date of Patent: Mar. 7, 2000

[54] MARKER AND IMMUNOLOGICAL REAGENT FOR DIALYSIS-RELATED AMYLOIDOSIS, DIABETES MELLITUS AND DIABETES MELLITUS COMPLICATIONS

[75] Inventors: Noriko Matsuda; Hisahiko Iwamoto; Naohiro Hanyu, all of Tokuyama, Japan

[73] Assignee: Tokuyama Corporation, Japan

[21] Appl. No.: 08/957,647

[22] Filed: Oct. 24, 1997

[30] Foreign Application Priority Data

Oct. 30, 1996 [JP] Japan ................................. 8-288380
Dec. 25, 1996 [JP] Japan ................................. 8-345137

[51] Int. Cl.[7] .......................... G01N 33/53; G01N 33/72; C07K 16/18
[52] U.S. Cl. .......................... 435/7.1; 435/7.8; 435/7.93; 435/14; 435/343; 436/518; 436/67; 436/811; 530/389.6; 530/388.7
[58] Field of Search .......................... 435/7.1, 7.8, 7.94, 435/7.95, 7.93, 14, 70.21, 172.2, 975, 331, 343, 337; 436/503, 518, 67, 86, 87, 88, 811; 530/388.2, 388.25, 388.7, 389.1, 389.3, 389.6

[56] References Cited

U.S. PATENT DOCUMENTS

| 5,610,076 | 3/1997 | Founds et al. .......................... 436/518 |
| 5,624,804 | 4/1997 | Bucala .......................... 435/7.1 |
| 5,698,197 | 12/1997 | Founds et al. .......................... 424/145.1 |

FOREIGN PATENT DOCUMENTS

WO93/13421  7/1993  WIPO.

OTHER PUBLICATIONS

T. Niwa et al., *Kidney International*, 50(4), 1303–1309 (1996).

M. Eulitz et al., *Biol. Chem. Hoppe–Seyler*, 366(9), 907–915 (1985).

M. Eulitz et al., *Biol. Chem. Hoppe–Seyler*, 368(7), 863–870 (1987).

S. Reddy et al., *Biochemistry*, 34(34), 10872–10878 (1995).

Horiuchi et al., 1991. Immunochemical approach to characterize advanced glycation end products of the Maillard reaction. J. Biological Chem. 266(12): 7329–7332, Apr. 1991.

V. Monnier et al., *New England J. Med.*, 314(7), 403–408 (1986).

M. Ahmed et al., *J. Biol. Chem.*, 261(11), 4889–4894 (1986).

J. Dunn et al., *Biochemistry*, 30(5), 1205–1210 (1991).

S. Reddy et al., *55th US Diabetes Mellitus Academic Society Meeting*, p. 115A, Abstract No. 431 (1995).

T. Miyata et al., *J. Clin. Invest.*, 92, 1243–1251 (Sep. 1993).

*Primary Examiner*—Christopher L. Chin
*Assistant Examiner*—James L. Grun
*Attorney, Agent, or Firm*—Wenderoth, Lind & Ponack, L.L.P.

[57] ABSTRACT

There are provided: an immunological reagent for diagnosis of or the evaluation of the effect of a medicine for dialysis-related amyloidosis, which includes an antibody which reacts specifically with a carboxymethylated α-amino acid, a carboxymethylated protein, or a carboxymethylated peptide; or, an immunological reagent for diagnosis of or the evaluation of the effect of a medicine for diabetes mellitus and diabetes mellitus complications, which includes an antibody which reacts specifically with an $N^{\alpha}$-carboxymethylated α-amino acid, an $N^{\alpha}$-carboxymethylated protein, or an $N^{\alpha}$-carboxymethylated peptide. Methods using the immunological reagents are provided: for determination of carboxymethylated hemoglobin as a marker for dialysis-related amyloidosis; or, for determination of $N^{\alpha}$-carboxymethylated hemoglobin as a marker for diabetes mellitus or diabetes mellitus complications.

6 Claims, 5 Drawing Sheets

CML-Hb LEVELS

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
      (A) LENGTH: 7 amino acids
      (B) TYPE: amino acid
      (C) STRANDEDNESS: single
      (D) TOPOLOGY: linear (xi) SEQUENCE DESCRIPTION: SEQ ID NO:1:

Val His Leu Thr Pro Glu Glu
1             5

MARKER AND IMMUNOLOGICAL REAGENT FOR DIALYSIS-RELATED AMYLOIDOSIS, DIABETES MELLITUS AND DIABETES MELLITUS COMPLICATIONS

DETAILED DESCRIPTION OF THE INVENTION

This invention relates to a marker and an immunological reagent for dialysis-related amyloidosis, diabetes mellitus and diabetes mellitus complications. More specifically, it relates to a marker useful for the diagnosis of or for the evaluation of the effect of a medicine for dialysis-related amyloidosis, diabetes mellitus and diabetes mellitus complications, and an immunological reagent for diagnosis of or for the evaluation of the effect of a medicine for dialysis-related amyloidosis, diabetes mellitus and diabetes mellitus complications.

It is known that protein in the blood reacts non-enzymatically with glucose to be glycated and becomes glycated protein. The glycation reaction is called the "Maillard reaction" and is divided into former-stage and latter-stage reactions. The former-stage reaction is defined a stage that the side-chain amino group or N-terminal amino group of protein reacts with the carbonyl group of saccharide to produce an Amadori rearranged compound through a Schiff base. As the former-stage reaction products are known hemoglobin A1C, glycated albumin and the like, and it is known that they are used as a clinical marker for diabetes mellitus.

It is also known that, after the above former-stage reaction, the Amadtori rearranged compound produced in the side chain amino group of protein changes in two directions. One of them is a reaction accompanied by at least one of fluorescence, browning and intramolecular or/and intermolecular crosslinking (also referred to as "latter-stage reaction A" hereinafter) and the other is an oxidative cleavage reaction (also referred to as "latter-stage reaction B" hereinafter) in which oxygen and a transition metal take part.

Whereas a final product of the Maillard reaction may be called "AGE" (Advanced Glycation End products), the term "AGE" generally, in most cases, refers to a product of a reaction accompanied by at least one of three characteristic phenomena (fluorescence, browning and intramolecular or/and intermolecular crosslinking) which are seen in the above latter-stage reaction A. Opinion is divided on whether or not the product of a reaction not accompanied by all the above three phenomena should also be referred to as AGE. That is, in addition to the above definition, there are various opinions on the definition of AGE, such as one asserting that AGE should refer to all the products obtained when glucose and protein are incubated in vitro at 37° C. for 60 days or more (which is a model reaction of the Maillard reaction), one asserting that AGE should refer only to products having biological activity to cause diabetes mellitus complications out of the above products, and the like,. There is no established definition of the term at the academic society. To avoid the above confusion, when the term "AGE" is used in this specification, it refers only to the product of a reaction (namely, the product of the latter-stage reaction A) accompanied by at least one of fluorescence, browning and intramolecular or/and intermolecular crosslinking out of the products of the Maillard reaction.

The product of the above latter-stage reaction A, that is, AGE, is considered to be an aggregate of a plurality of compounds. At present, pyrraline, pentosidine, closslines A&B, X1 and the like are proposed as AGE structures and are qualitatively and quantitatively determined by the measurement of fluorescence intensity or an antigen-antibody reaction. As for the latter-stage reaction A for generating AGE, it has been reported that it takes place in vivo and takes part in the occurrence of complications based on vascular dysfunction (Monnier, V. M., et al, New England Journal of Medicine, vol.314, p.403, 1986). Attention is being paid to AGE as being related to the occurrence and progress of complications in diabetes mellitus patients, and it has been also reported that AGE has biological activity related to the occurrence and progress of diabetes mellitus complications (Morisaki et al, "Saishin Igaku (The Latest Medical Science)", vol.49, p.248, 1994).

Meanwhile, it has been reported that $N^\epsilon$-carboxymethyllysine (sometimes, may be abbreviated as "CML" hereinafter) whose amino group at the E-position is carboxymethylated is identified as the product of the other reaction (latter-stage reaction B) in the latter stage of the Maillard reaction (Ahmed, M. U., et al, Journal of Biological Chemistry, vol.261, p.4889, 1986) and that CML is present in the lens proteins and skin collagen of the aged and the diabetes mellitus patients (Dunn, J. A., et al, Biochemistry, vol.30, p.1205, 1991). It has been also reported that a substance in which a hydrogen atom of the side-chain amino group of bovine serum albumin (to be abbreviated as "BSA" hereinafter) is substituted with a carboxymethyl group (sometimes, may be referred to as "carboxymethylated" hereinafter) greatly inhibits a reaction between AGE and an anti-AGE antibody (the Abstract of the 55-th US Diabetes Mellitus Academic Society's Meeting, p.115A, 1995).

However, there are no reports on protein or peptide whose N-terminal only is carboxymethylated (sometimes, may be referred to as "carboxymethylated product" hereinafter). The difference of the proportion and quantity of the substituted protein or peptide in protein or peptide in vivo, particularly in a body fluid, between a diabetes mellitus patient or a diabetes mellitus patient who has occurrence of a complication such as nephropathy or retinopathy (sometimes, may be referred to as "a diabetes mellitus complication patient" hereinafter) and a healthy person has not been known, and the utility of the protein or peptide, particularly, utility as a marker for diabetes mellitus or diabetes mellitus complications has not been recognized.

Meanwhile, dialysis-related amyloidosis (sometimes, may be simply referred to as "DRA" hereinafter) is an amyloid thesaurosis which is a complication seen in a patient having a long-term dialysis treatment and which mainly causes carpal tunnel syndrome and lytic bone lesions.

In recent years, it has been found that a main component of deposited amyloid is β2 microglobulin (to be abbreviated sometimes as "β32M" hereinafter) and that amyloid containing β2M as a precursor protein is deposited on a joint synovia to cause carpal tunnel syndrome, multiple arthritis, destructive spinal cord arthrosis and the like. However, there is no correlation between the occurrence of dialysis-related amyloidosis and the concentration of β2M in the blood and it has been suggested that factors other than the concentration of β2M in the blood are related with the occurrence of the dialysis-related amyloidosis. Of these, particular attention is paid to β2M modified products, and studies on the β2M modified products are under way. Miyata et al. have recently found that the product of the latter-stage Maillard reaction of protein (AGE) is present in deposited amyloid, confirmed β2M having a pentosidine structure and a carboxymethyllysine structure as the AGE (to be abbreviated as "AGE-β2M" hereinafter) and suggested the possibility that the AGE-β2M may be involved in the progress of bone or joint lesions (J. Clin. Invest. vol. 92, pp.1243–1252, 1993 and "Rinsyou Toseki (Clinical Dialysis)", vol. 12, no. 8, pp. 1163–1170, 1996).

However, it cannot be said that the details of the causes and morbity of DRA have been completely elucidated, and its fundamental prevention and treatment measures are yet to be established. Therefore, importance is attached to the retardation of the progress of a disease with an appropriate treatment through accurate and early diagnosis.

As described above, it is extremely important to diagnose DRA in its early stage. However, a conventional diagnosis method has problems in accuracy and demands on a subject.

In other words, DRA has been heretofore diagnosed with Congo Red staining of mainly a tissue of a site showing a symptom as a specimen. However, this diagnosis method has a problem in that a patient suffers physical pain or injury. It also involves such a problem that in some cases, the specimen cannot be stained by Congo Red even when it apparently shows symptoms of DRA clinically.

Hence, in recent years, attempt as a more accurate and non-invasive method has been made to diagnose DRA by labeling β2M in vivo with a radioactive isotope and then, obtaining an image of an amyloid deposition site with a scintillation camera or the like. However, even this diagnosis method has such problems that the influence of the isolation or accumulation of a labeling radioactive isotope on a living body is large and that procedures in the above method are troublesome.

As described above, although various studies on the mechanism of the occurrence of DRA are under way, there are no known examples in which findings obtained from these studies have been actually applied to a new diagnosis method solving the problems of the above diagnosis methods. For instance, Miyata el al. have concluded from their studies that AG-β2M takes part: in the occurrence of DRA but have not investigated the correlation between the concentration of AG-β2M in body fluids such as blood, urine and lymph and the occurrence of DRA. In other words, it is totally unknown whether or not AGE-β2M can be used as a marker for DRA effectively. It is an object of the present invention to provide a marker for dialysis-related amyloidosis (DRA).

It is another object of the present invention to provide an immunological reagent for the diagnosis of DRA, comprising an antibody which reacts specifically with the above marker (to be referred to as "first marker" hereinafter) of the present invention.

It is still another object of the present invention to provide an immunological reagent for the evaluation of the effect of a medicine for the treatment or prevention of DRA, comprising an antibody which reacts specifically with the above marker of the present invention.

It is a further object of the present invention to provide a marker for diabetes mellitus or diabetes mellitus complications (to be referred to as "second marker" hereinafter).

It is a still further object of the present invention to provide an immunological reagent for the diagnosis of diabetes mellitus or diabetes mellitus complications, comprising an antibody which reacts specifically with the second marker of the present invention.

It is a still further object of the present invention to provide an immunological reagent for the evaluation of the effect of a medicine for the treatment or prevention of diabetes mellitus or diabetes mellitus complications, comprising an antibody which reacts specifically with the second marker of the present invention.

Other objects and advantages of the present invention will become apparent from the following description.

DETAILED DESCRIPTION OF THE EMBODIMENT

Figure 1:
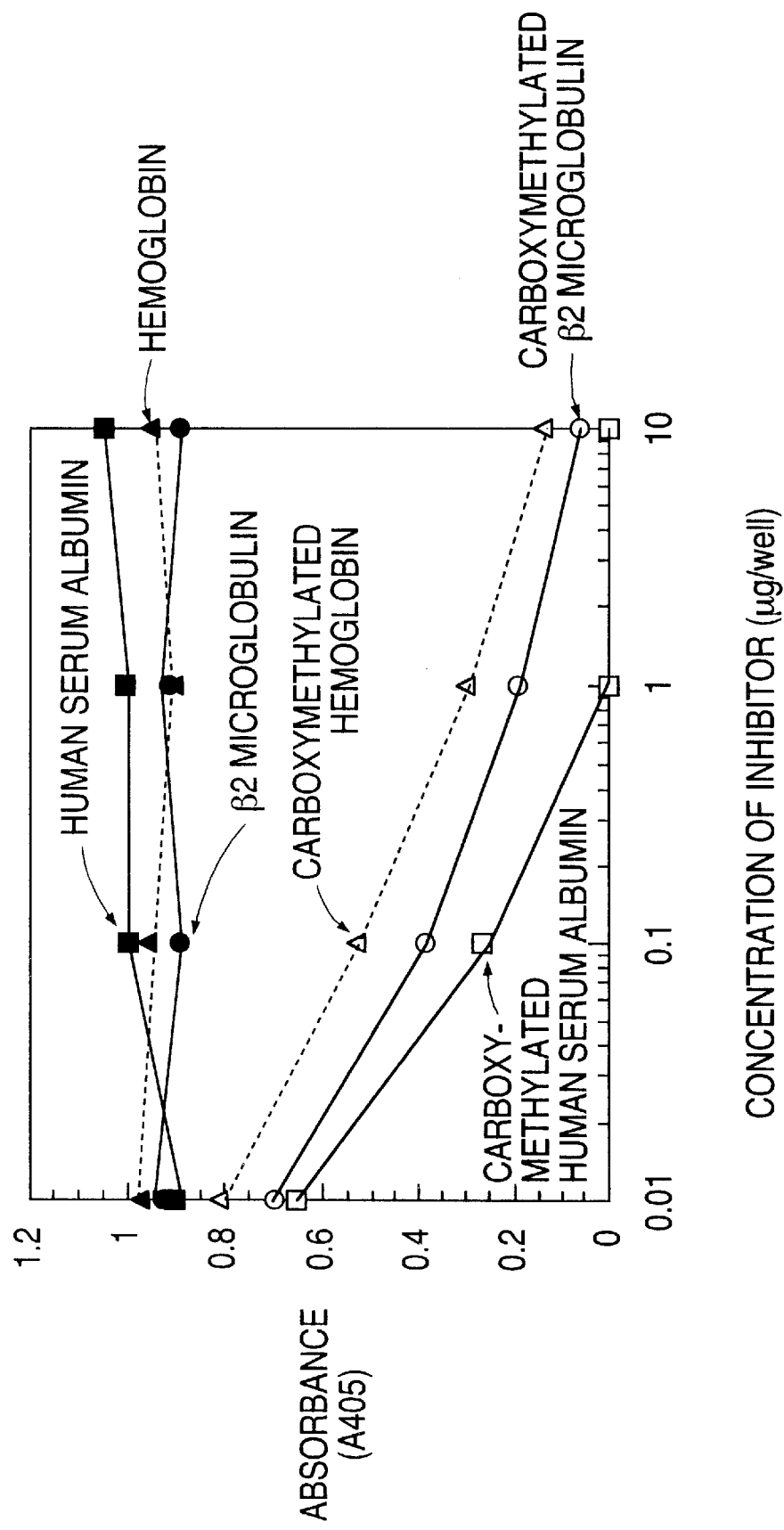
FIG. 1 is a graph showing the measurement results of the antigen specificity of an antibody against a prepared carboxymethylated human serum albumin in accordance with a competitive ELISA method, in which the axis of ordinates shows absorbance at 405 nn and the axis of abscissas shows the amount of each inhibitor added.

How the inventors of the present invention have attained the above objects and advantages of the present invention and their findings will be briefly described hereinafter.

That is, firstly, the present inventors have taken notice of the fact that AGE has unique physiological activity, considered that AGE could be a marker for DRA, and conducted various studies on the relationship between AGE in vivo and the occurrence of DRA. As a result, they have found that there are significant differences in the concentration of the specific protein in vivo or the average number of the specific substituent groups present in one molecule of the specific protein between a DRA patient and a healthy person in relation with AGE having a specific substituent group (that is, protein having a specific substituent group), and that the amount of the specific protein in a specimen and the average number of the specific substituent groups present in one molecule of the specific protein can be measured easily with a reagent comprising an antibody which reacts specifically with the specific protein. The present invention has been accomplished by these findings.

Secondly, the present inventors have found that there is a significant difference in the carboxymethylation rate defined by the following equation of a certain protein in a body fluid between a case of diabetes mellitus or diabetes mellitus complications and a healthy person and that the carboxymethylated protein can be used as a marker for diabetes mellitus or diabetes mellitus complications effectively. Thus, the present invention has been accomplished by this finding. In the present specification, the carboxymethylation rate is defined by the following equation for all the specific kinds of proteins or peptides present in a body fluid as a specimen (no matter whether a specific kind of protein or peptide is modified by carboxymethylation or not) and is an index indicating how many N-terminals of the specific protein or peptide are carboxymethylated on the average.

carboxymethylation rate (%)=(total number of carboxymethyl groups present at N-terminals of the specific protein or peptide)/(total number of N-terminals present in the specific protein or peptide)×100

According to the present invention, firstly, the above objects and advantages of the present invention can be attained by use of one member selected from the group consisting of a carboxymethylated α-amino acid in which an amino group(s) of an α-amino acid is(are) carboxymethylated, a carboxymethylated protein in which at least one of amino acid units constituting a protein is carboxymethylated and a carboxymethylated peptide in which at least one of amino acid units constituting a peptide is carboxymethylated as a marker for dialysis-related amyloidosis.

The α-amino acid used as a marker in the present invention may be a carboxylic acid in which a carboxyl group and a amino group are bonded to the same carbon, and is preferably one of 20 kinds of amino acids constituting natural protein.

The protein used as a marker in the present invention is not limited to a particular one if it is a protein in vivo. Illustrative examples of the protein include simple proteins such as albumin, β2M and histone; glycoproteins such as collagen, γ-globulin and erythrocyte peripheral membrane proteins; lipoproteins such as low-density lipoproteins and high-density lipoproteins; metal proteins such as hemoglobin and transferrin. Preferably, it is a protein derived from a body fluid which can be extracted easily from a subject as a specimen. Of the proteins derived from body fluids, hemoglobin which has long life and a high concentration in the blood and β2M which is a main component of deposited amyloid are particularly preferred.

The peptide used as a marker in the present invention is not limited to a particular one if it is a peptide in vivo and may be an oligopeptide or polypeptide, as exemplified by products obtained by the degradation of the above proteins.

The term "carboxymethylated α-amino acid" (sometimes, to be simply referred to as "carboxymethylated product" hereinafter) as used in the present specification denotes an α-amino acid in which an amino group(s) of an α-amino acid is(are) carboxymethylated. When the a-amino group(s) is(are) carboxymethylated, 20 kinds of amino acids constituting natural protein are preferably used whereas when an amino group(s) other than the a-amino group(s) is(are) carboxymethylated, basic amino acids constituting natural protein are preferably used. The basic amino acids include lysine, arginine and the like.

The term "carboxymethylated protein or carboxymethylated peptide" (sometimes, may be referred to as "carboxymethylated product" hereinafter) as used in the present specification denotes a protein or peptide in which at least one of amino groups of amino acid units constituting a protein or peptide are carboxymethylated. The amino groups to be carboxymethylated are side-chain amino groups or N-terminal amino groups of lysine or the like and do not include —NH— present in the amino bond.

As shown in Examples which will be described later, the amount of a carboxymethylated product present in the body of a DRA patient and the average number of carboxymethyl groups present in one molecule of the carboxymethylated product (may be simply referred to as "carboxymethylation rate" hereinafter) are much higher than those of a healthy person (see Tables 1, 2 and 3 given later). Therefore, the carboxymethylated product used in the present invention can be used as a marker for DRA in the field of clinical examination. That is, it is possible to judge whether a person has occurrence of DRA or to forecast the occurrence or progress of DRA by measuring the carboxymethylation rate and amount of the carboxymethylated product in vivo, particularly in the blood. In Example 1 which will be described later, since carboxymethylated hemoglobin is used as the carboxymethylated product and an absolute amount of hemoglobin of a DRA patient is smaller than that of a healthy person because the DRA patient undergoes artificial dialysis, the correlation between the occurrence of DRA and the concentration of the carboxymethylated product in the specimen is not investigated. However, as shown in Example 2, the favorable correlation between the concentration of the carboxymethylated product (carboxymethylated β2M) in the specimen of a DRA patient and the concentration of the carboxymethylated product in the specimen of a healthy person is seen.

Whereas a method for directly measuring the amount or carboxymethylation rate of a carboxymethylated product in vivo (such as in the blood or urine) is unknown, a method for indirectly measuring the amount of a carboxymethylated product by degrading a carboxymethylated product to obtain a carboxymethylated amino acid and measuring the amount of the carboxymethylated amino acid is already known. For example, there are known a method comprising hydrolyzing a carboxymethylated product and detecting a carboxymethylated amino acid using liquid chromatography/mass spectrometry, a method comprising hydrolyzing a carboxymethylated product and detecting a carboxymethylated amino acid using gas chromatography/mass spectrometry, and so forth. However, these indirect measurement methods have such problems as a complicated operation and low sensitivity, and hence, a direct measurement method which facilitates measurement and has high sensitivity has been desired. Under the circumstances, the present inventors have developed a method for detecting a carboxymethylated product in vivo making use of an antigen-antibody reaction using an antibody (may be simply referred to as "anti-CM antibody" hereinafter) which reacts specifically with a carboxymethylated product.

The anti-CM antibody is obtained by using a carboxymethylated product synthesized by an organic synthesizing technique as an immunogen (antigen). A protein which is a starting material for synthesizing such a carboxymethylated product is not limited to a particular one, as exemplified by simple proteins such as albumin, 32M and histone; glycoproteins such as collagen, Y-globulin and erythrocyte peripheral membrane proteins; lipoproteins such as low-density lipoproteins and high-density lipoproteins; composite proteins such as metal proteins including hemoglobin and transferrin.

When a peptide is used as a starting material for synthesizing a carboxymethylated product, the peptide may be an oligopeptide or polypeptide, as exemplified by products obtained by the degradation of the above proteins, products obtained by artificially synthesizing a specific area of the above proteins, and the like.

As a method for carboxymethylating an amino group(s) of an a -amino acid or an amino group of amino acid constituting the above protein or peptide, that is, a method for substituting the hydrogen of the above amino group with a group —$CH_2$—COOH can be used any known methods without restriction. For example, like a reduction alkylation method described in "SHIN SEIKAGAKU JIKKEN KOUZA 1, TANPAKUSHITSU 4 (New Biochemical Experiment Lecture 1, Protein 4)" (edited by the Japanese Biochemical Society, pp.13-16, Tokyo Kagaku Dojin, published on Mar. 20, 1991), a method is preferred in which an aldehyde compound represented by CHO—COOH and a protein or peptide are dissolved in an aqueous solution such as a borate buffer solution or phosphate buffer solution and are caused to react with each other at a pH value of 8 to 10 in the presence of a hydrogenated product-reducing agent such as sodium borohydride or sodium cyanoborohydride. At a pH value higher than 10, the protein or the like may be Denatured, while at a pH value lower than 8, the hydrogenated product-reducing agent becomes unstable. To proceed with the reaction specifically and quantitatively, the reaction temperature is preferably 0 to 10° C. Alternatively, a carboxymethylated product can be obtained by incubating reduced sugar and a protein at 37° C. for 60 days in an aseptic condition in the presence of oxygen.

The thus obtained carboxymethylated product is generally water-soluble and precipitates by the addition of acetone, alcohol, ammonium sulfate, heavy metal salt or the like. The above carboxymethylated product can be detected by a known method other than a method for detecting an amino group, such as an ultraviolet absorption method, dye binding method, phenol reagent method or the like. In the above methods, a substance having an amino group such as protein, lipid, saccharide or the like is easily carboxymethylated, whereas, in the protein or peptide, the side chain or N-terminal amino groups of lysine are easily carboxymethylated selectively.

A method for obtaining an anti-CM antibody using the thus synthesized carboxymethylated product as an antigen is not limited to a particular one and a method for immunizing a host animal to a carboxymethylated product as an antigen may be optionally employed.

In this respect, the antigen is not particularly limited if it is EL carboxymethylated product. When a carboxymethylated peptide is used as the antigen, a carboxymethylated peptide bound to a conventionally known carrier protein such as hemocyanin, bovine serum albumin, β-galactosidase or the like is preferably used as the antigen because it has extremely low capacity to induce immune response in some cases. To bind the carboxymethylated peptide to a carrier protein, a method used for this purpose is generally used without restriction.

The derivation of an antibody formed from the antigen is not particularly limited. An antiserum, ascites fluid or the like obtained by immunizing a host animal such as a rabbit, goat, mouse or guinea pig to a carboxymethylated product, purified by dialysis, centrifugal concentration, liquid chromatography or the like, as an antigen can be used directly or as a polyclonal antibody through purification by a conventionally known method such as a salting-out method, gel filtration method, ion exchange chromatography, affinity chromatography or (electrophoresis. Alternatively, a monoclonal antibody prepared from a hybridoma obtained by fusing an antibody producing cell such as a spleen cell or lymphocyte cell of a mammal sensitized by an antigen with a myeloma cell can be used directly or through purification by a conventionally known method such as a salting-out method, gel filtration method, ion exchange chromatography, affinity chromatography or electrophoresis.

To prepare an immunological reagent, these antibodies may be used directly, while active fragments (portions including an antigen-recognition site of an antibody), such as Fab, Fab' or F(ab')2, of antibodies obtained by treating the above antibodies with an enzyme may be used as an anti-CM antibody.

According to the present invention, there is also provided an immunological reagent for the diagnosis of dialysis-related amyloidosis, which comprises at least one member selected from the group consisting of an antibody which reacts specifically with a carboxymethylated α-amino acid in which an amino group(s) of an α-amino acid is(are) carboxymethylated, an antibody which reacts specifically with a carboxymethylated protein in which at least one of amino acid units constituting a protein is carboxymethylated, and an antibody which reacts specifically with a carboxymethylated peptide in which at least one of amino acid units constituting a peptide is carboxymethylated.

The "immunological reagent" of the present invention is not limited to a particular kind if it can detect a carboxymethylated product, making use of an antigen-antibody reaction between an anti-CM antibody and a carboxymethylated product. For example, an anti-Cm antibody, an antibody against a bio component(s) such as β2M or hemoglobin and a carboxymethylated product can be carried on a suitable insoluble carrier to cope with such methods as a non-competitive method, competitive method, sandwich method or the like which will be described later. The carboxymethylated product can be measured by detecting an antigen-antibody reaction caused by bringing the immunological reagent into contact with an antigen and/or anti-CM antibody in the specimen in accordance with a measurement method. This antigen-antibody reaction can be detected by making use of the agglutination of the insoluble carrier when the immunological reagent of the present invention is a so-called immunoagglutination reagent. When the immunological reagent of the present invention is a so-called labeling immunoassay reagent, the antigen-antibody reaction can be detected as a change in the physical amount of colorimetry, luminescence or fluorescence or the like.

As for illustrative examples of the immunological reagent of the present invention, qualitative reagents include a latex agglutination reagent, microtiter agglutination reagent and the like, whereas quantitative reagents include a radioimmunoassay reagent, enzyme immunoassay reagent, fluorescent immunoassay reagent, chemical luminescence immunoassay reagent, latex quantitative reagent and the like.

As for the form of the insoluble carrier carrying an anti-CM antibody or antibody against a bio component(s), or a carboxymethylated product in a specimen, a suitable form may be selected according to application purpose. For example, it may be in a form of bead, test plate, disk, or filter or in a spherical or tubular form. As the material of the above carrier may be used ones which are generally used as an immunoassay carrier, such as glass, polysaccharide and derivatives thereof, silica gel, porous ceramics, metal oxides, erythrocyte, synthetic resins such as propylene, styrene, acrylamide and acrylonitrile, and these synthetic resins having reactive functional group(s) such as a sulfone group and amino group introduced thereto by a known method.

As a method for immobilizing an anti-CM antibody or antibody against a bio component(s) or an antigen in a specimen onto the insoluble carrier may be used known methods such as a physical adsorption method, covalent bonding method, ionic binding method, crosslinking method and the like without restriction.

The basic operation for measuring a carboxymethylated product with a labeling immunoassay reagent can be conducted in accordance with a conventional detection method such as enzyme immunoassay (EIA), e.g., radioimmunoassay (RIA), ELISA method, western blotting method, a dot blotting method or the like. The operation and procedure in each of the above detection methods do not differ from those generally employed and can be based on a known non-competitive method, competitive method, sandwich method or the like. In the non-competitive method, after a carboxymethylated product or anti-CM antibody in a specimen has been carried on an insoluble carrier, it may be contacted with an anti-CM antibody or carbosymethylated product. In the competitive method, after an artificially manufactured carboxymethylated product has been carried on an insoluble carrier, it may be contacted with an anti-CM antibody which has been reacted with a carboxymethylated product in a specimen. In the sandwich method, after an anti-CM antibody or antibody against a bio component(s) such as β2M or hemoglobin has been carried on an insoluble carrier, it may be contacted to an antigen in a specimen and then to an antibody against a bio component(s) or an anti-CM antibody. The carboxymethylation rate of a protein or peptide or the amount of a carboxymethylated product can be measured by these methods.

Examples of the labeling agent for use in the labeling immunoassay reagent are radioactive substances such as radioactive iodine and radiocarbon; fluorescent substances such as fluorescein isothiocyanate and tetramethyl rhodamine; enzymes such as alkaline phosphatase and peroxidase; and the like. The antigen-antibody reaction product obtained by the above method is detected making use of radioactivity, colorimetry, fluorescence, luminescence or the like.

For instance,, an anti-CM antibody or an antigen in a specimen is carried on an insoluble carrier in an amount of 0.01 to 1,000 $\mu g/cm^2$ and brought into contact with 0.001 to 1,000 $\mu g$ of an anti-CM antibody or an antigen in a specimen for measurement. When the antibody against a bio component(s) is carried on an insoluble carrier, it is brought into contact with an antigen in a specimen and then with an anti-CM antibody as described above. As the antibody not carried on the insoluble carrier is preferably used an antibody labeled with a labeling agent.

The basic operation for measuring a carboxymethylated product with an immunoagglutination reagent can be conducted in accordance with a conventional detection method such as a hemaagglutination reaction method, passive agglutination reaction method, nephelometric immunoassay, turbidimetric immunoassay or the like. For instance, particles (to be referred to as "sensitized particles" hereinafter) carrying 0.001 to 100 mg of an anti-CM antibody per 1 g of a particulate insoluble carrier by the above method may be used as an effective component of an immunological reagent by dispersing them in an aqueous medium so that they are contained in an amount of 0.001 to 15% by weight. The average particle diameter of the insoluble carrier carrying the antibody is preferably 0.05 to 10 $\mu m$ from a viewpoint of easy occurrence of agglutination after an antigen-antibody reaction and easy judgment of the agglutination. The sensitized particles prepared by the above method are brought into contact with an antigen in a specimen to measure the degree of agglutination of the sensitized particles. The degree of agglutination of the particles can be measured visually or by a known optical measurement or other conventional method.

When the immunological reagent of the present invention is used as a diagnostic reagent, the concentration of a carboxymethylated product in a specimen or the carboxymethylation rate of the carboxymethylated product is measured using an anti-CM antibody. Illustrative examples of the bio component as the specimen include body fluids such as blood, urine, lymph, amniotic fluid, marrow liquid and saliva; extracellular matrices such as skin collagen and fibronectin, tissues such as lens proteins, artery and kidney; and the like. Body fluids often used as a specimen for clinical examination are more preferable.

When a reduction in the amount or carboxymethylation rate of a carboxymethylated product contained in a specific bio component is measured by administering a DRA treatment medicine, the effect of the treatment medicine can be evaluated using the immunological reagent of the present invention.

That is, according to the present invention, there is further provided an immunological reagent for the evaluation of the effect of a medicine for the treatment or prevention of dialysis-related amyloidosis, comprising at least one member selected from the group consisting of an antibody which reacts specifically with a carboxymethylated α-amino acid in which an amino group(s) of an α-amino acid is(are) carboxymethylated, an antibody which reacts specifically with a carboxymethylated protein in which at least one of amino acid units constituting a protein is carboxymethylated, and an antibody which reacts specifically with a carboxymethylated peptide in which at least one of amino acid units constituting a peptide is carboxymethylated.

According to the present invention, secondly, the above objects and advantages of the present invention are attained by use of one member selected from the group consisting of an $N^{\alpha}$-carboxymethylated α-amino acid in which the α-amino group of an α-amino acid is carboxymethylated, an $N^{\alpha}$-carboxymethylated protein in which the N-terminals of a protein are carboxymethylated, and an $N^{\alpha}$-carboxymethylated peptide in which the N-terminals of a peptide are carboxymethylated as a marker for diabetes mellitus or diabetes mellitus complications.

Illustrative Examples of the α-amino acid, protein and peptide used as a marker (second marker) in the present invention are the same as those listed for the first marker.

Whereas a method for directly measuring the carboxymethylation rate of a protein (for example, a protein in the blood or urine) or peptide in vivo is not available yet, a method for indirectly measuring an carboxymethylated amino acid by the degradation of a carboxymethylated product is already known. Illustrative examples of the measurement method include one for detecting a carboxymethylated amino acid with a liquid chromatography/mass spectrometry by hydrolyzing a carboxymethylated product; one for detecting a carboxymethylated amino acid with a gas chromatography/mass spectrometry by hydrolyzing a carboxymethylated product; and the like. However, the method for indirectly measuring a carboxymethylated product has problems that the operation is complicated and the sensitivity is low. Therefore, a direct measurement method which facilitates measurement and has high sensitivity has been desired. Under the circumstances, the present inventors have developed a method for conducting a carboxymethylated product in vivo making use of an antigen-antibody reaction using the anti-CM antibody.

The anti-CM antibody is obtained by using a carboxymethylated product synthesized by an organic synthesizing technique as an immunogen (antigen). A protein which is a starting material for synthesizing such a carboxymethylated product is not limited to a particular one, as exemplified by simple proteins such as albumin, β2M and histone; glycoproteins such as collagen, γ-globulin and erythrocyte peripheral membrane proteins; lipoproteins such as low-density lipoproteins and high-density lipoproteins; composite proteins such as metal proteins including hemoglobin and transferrin.

When a peptide is used as a starting material for synthesizing a carboxymethylated product, the peptide may be an oligopeptide or polypeptide, as exemplified by products obtained by the degradation of the above proteins, products obtained by artificially synthesizing a specific area of the above proteins, and the like.

As a method for carboxymethylating an amino group(s) of an α-amino acid or amino groups present at N-terminals of an amino acid constituting the above protein or peptide, that is, a method for substituting the hydrogen of the above amino group with a group —$CH_2$—COOH can be used any known methods without restriction. For example, as described above, a method is employed in which an aldehyde compound represented by CHO—COOH, an α-amino acid and a protein or peptide are dissolved in an aqueous solution such as a borate buffer solution or phosphate buffer solution and are caused to react with each other at a pH value of 8 to 10 in the presence of a hydrogenated product-reducing agent such as sodium borohydride or sodium cyanoborohydride, and then, an $N^{\alpha}$-carboxymethylated α-amino acid or a carboxymethylated protein or peptide (carboxymethylated product) in which only amino groups at N-terminals are carboxymethylated may be dispensed by ion chromatography or the like.

In the above reaction, at a pH value higher than 10, the protein or the like may be denatured and at a pH value lower than 8, the hydrogenated product-reducing agent becomes unstable. To proceed with the reaction specifically and quantitatively, the reaction temperature is preferably 0 to 10° C. Alternatively, a carboxymethylated product can be obtained by incubating reduced sugar and a protein at 37° C. for 60 days in an aseptic condition in the presence of oxygen.

The carboxymethylated a -amino acid, protein or peptide obtained through the above reaction is generally water-soluble and precipitates by the addition of acetone, alcohol, ammonium sulfate, heavy metal salt or the like. The above carboxymethylated product can be detected by a known method other than a method for detecting an amino group, such as an ultraviolet absorption method, dye binding method, phenol reagent method or the like. In the above methods, a substance having an amino group such as protein, lipid, saccharide or the like is easily carboxymethylated whereas, in the protein or peptide, the side chain or N-terminal amino groups of lysine are easily carboxymethylated selectively. In the above reaction, a carboxymethylated product in which only amino groups present at the side chains of lysine or amino groups at N-terminals and side chains of lysine are carboxymethylated is obtained in addition to a carboxymethylated product in which only amino groups at N-terminals are carboxymethylated. Therefore, when the carboxymethylated product is dispensed from the above reaction product by an ion chromatography or the like and used as an antigen, an anti-CM antibody is obtained. In the above reaction, when a carboxymethylated protein or peptide in which amino groups are present only at N-terminals is used (having no amino groups at side chains), a carboxymethylated product having high purity can be obtained efficiently and an anti-CM antibody can be obtained easily.

It should be understood that a description of the first marker is directly applied to an antigen for preparing the anti-CM antibody or an antibody prepared using the antigen.

According to the present invention, therefore, there is also provided an immunological reagent for the diagnosis of diabetes mellitus or diabetes mellitus complications, comprising at least one member selected from the group consisting of an antibody which reacts specifically with an $N^\alpha$-carboxymethylated $\alpha$-amino acid in which the $\alpha$-amino group of an $\alpha$-amino acid is carboxymethylated, an antibody which reacts specifically with an $N^\alpha$-carboxymethylated protein in which -the N-terminals of a protein are carboxymethylated, and an antibody which reacts specifically with an $N^\alpha$-carboxymethylated peptide in which the N-terminals of a peptide are carboxymethylated.

It should be understood that a description of the immunological reagent for the diagnosis of dialysis-related amyloidosis is directly applied to matters are not described herein, such as the form of this immunological reagent, the detection of an antigen-antibody reaction, specific examples of the immunological reagent, an insoluble carrier carrying an antibody or antigen, a method for immobilizing an antibody or antigen on this carrier, the basic measurement operation of a carboxymethylated product in a labeling immunoassay reagent or immunoagglutination reagent and the like.

Since the carboxymethylation rate of a protein present in the body of a case of diabetes mellitus or a case of diabetes mellitus complications is much higher than that of a healthy person (see Tables 5 to 7) as shown in Examples which will be described later, the carboxymethylated product used in the present invention can be used as a marker for diabetes mellitus or diabetes mellitus complications in the field of clinical examination. In other words, by measuring the carboxymethylation rate of a protein or peptide in vivo, particularly in a body fluid, it is possible to judge whether a person has occurrence of diabetes mellitus or diabetes mellitus complications or to forecast the progress of diabetes mellitus or the occurrence or progress of diabetes mellitus complications.

The above immunological reagent for diabetes mellitus or diabetes mellitus complications which makes use of an immunoassay method is used advantageously as a reagent for the diagnosis of diabetes mellitus or diabetes mellitus complications or a reagent for the evaluation of the effect of a medicine for the treatment or prevention of diabetes mellitus or diabetes mellitus complications.

When the reagent is used as a diagnostic reagent, the amount or proportion of an antigen in a specimen, that is, an $N^\alpha$-carboxymethylated $\alpha$-amino acid or a carboxymethylated protein or peptide in which N-terminal amino groups are carboxymethylated, contained in a specific bio component, is measured using an anti-CM antibody. Illustrative examples of the bio component include body fluids such as blood, urine, lymph, amniotic fluid, marrow liquid and saliva; extracellular matrices such as skin collagen and fibronectin, tissues such as lens proteins, artery and kidney; and the like. Body fluids often used as a specimen for clinical examination are more preferable.

When the reagent is used as a reagent for the evaluation of the effect of a medicine, a reduction in the amount or proportion of an $N^\alpha$-carboxymethylated $\alpha$-amino acid or a carboxymethylated protein or peptide in which N-terminal amino groups are carboxymethylated, contained in a specific bio component, is measured by administering a treatment medicine for diabetes mellitus or diabetes mellitus complications.

That is, according to the present invention, there is further provided an immunological reagent for the evaluation of the effect of a medicine for the treatment or prevention of diabetes mellitus or diabetes mellitus complications, comprising at least one member selected from the group consisting of an antibody which reacts specifically with an $N^\alpha$-carboxymethylated $\alpha$-amino acid in which the $\alpha$-amino group of an $\alpha$-amino acid is carboxymethylated, an antibody which reacts specifically with an $N^\alpha$-carboxymethylated protein in which the N-terminals of a protein are carboxymethylated, and an antibody which reacts specifically with an $N^\alpha$-carboxymethylated peptide in which the N-terminals of a peptide are carboxymethylated.

The following examples are provided for the purpose of further illustrating the present invention but are in no way to be taken as limiting.

EXAMPLE 1

(1) Preparation of carboxymethylated protein

To carboxymethylate the amino groups of a protein, 1 ml of a human serum albumin solution (Fraction V, a product of Sigma Co., Ltd.) having a pH value of 9 and a concentration of 1 mg/ml was mixed with 1 ml of 0.25 M glyoxylic acid (a product of Sigma Co., Ltd.) having a pH value of 9 and left to stand at 0° C. for 12 hours. Thereafter, 1 mg of sodium cyanoborohydride was added to the resulting mixture and left to stand for another 12 hours.

As a control, human serum albumin was treated in the same manner as described above except that glyoxylic acid was not added.

To obtain the carboxymethylation rate of the human serum albumin, the samples obtained above were hydrolyzed at 120° C. for 20 hours using a 6N hydrochloric acid and the amino acids of the samples were analyzed with an amino acid analyzer (Model 835, a product of Hitachi, Ltd.).

As a result, the formation of carboxymethylated lysine (to be simply referred to as "CML" hereinafter) was observed in the human serum albumin mixed with glyoxylic acid and the carboxymethylation rate of the human serum albumin was 12 mol %. On the other hand, the carboxymethylation rate of the human serum albumin not mixed with glyoxylic acid was 0 mol %.

The carboxymethylated human serum albumin obtained by the above method was dialyzed with a 20 mM phosphate buffer solution (PH: 7.4) at 4° C. for 2 days to remove unreacted portions of glyoxylic acid and sodium cyanoborohydride, and used as an immunogen for preparing an antibody against a carboxymethylated protein.

Further, commercial hemoglobin (a product of Sigma Co., Ltd.) was carboxymethylated in the same manner as described above. The result of amino acid analysis showed that the carboxymethylation rate of this carboxymethylated hemoglobin was 5 mol %.

(2) Preparation of antibody against carboxymethylated protein

A rabbit weighing 2 kg or more was immunized to the carboxymethylated human serum albumin prepared in Example 1 as an antigen in the following manner.

A mixture containing 0.5 ml of the antigen solution having a concentration of 2 mg/ml and 0.5 ml of Freund's complete adjuvant was injected into the ear vein of the rabbit. Thereafter, a mixture containing 0.25 ml of the antigen solution having a concentration of 2 mg/ml and 0.25 ml of Freund's incomplete adjuvant was additionally injected every two weeks. During this time, to confirm whether an antibody against carboxymethylated human serum albumin was produced, blood was partially drawn from the marginal ear vein of the rabbit once every two weeks. After six weeks, it was confirmed by an ELISA method that the antibody against the carboxymethylated human serum albumin was produced and all the blood was drawn.

(3) Preparation of affinity purification column 25 ml of Affi-gel 15 (a product of Bio-Rad Co., Ltd.) was washed with 75 ml of a 10 mM acetate buffer solution (PH: 4.5), and 62.5 ml of a human serum albumin solution having a concentration of 10 mg/ml was added and stirred gently at room temperature for 1 hour. Thereafter, an unreacted portion of human serum albumin was removed by filtration, 30 ml of a 1 M ethanolamine solution was added and stirred gently at room temperature, and an unreacted portion of N-hydroxysucciimide ester was blocked. A carrier having the human serum albumin immobilized was charged into a column and washed with ion exchange water until the absorbance thereof at 280 nm became 0. Further, the column was equilibrated with a 20 mM phosphate buffer solution (PH: 7.4) containing 0.15 M sodium chloride.

(4) Affinity purification of antibody against carboxymethylated human serum albumin The prepared antibody against carboxymethylated human serum albumin was diluted with a 20 mM phosphate buffer solution (PH: 7.4) containing 0.15 M sodium chloride so as to have a concentration of 1 mg/ml, and the diluted antibody was applied to the affinity purification column in an amount of about 100 mg. Thereafter, the phosphate buffer solution was flown at a flow rate of 0.5 ml/min until the absorbance thereof at 280 nm became 0. The antibody which was not bound to the column was collected as an antibody against carboxymethylated human serum albumin. When the absorbance at 280 nm became 0, the phosphate buffer solution was replaced by a 0.1 M glycine buffer solution (PH: 3.0), the antibody bound to the column was eluted, the column was equilibrated with a 20 mM phosphate buffer solution (PH: 7.4) containing 0.15 M sodium chloride. The collected antibody was applied to the column again, and the antibody not bound to the column was collected. This operation was repeated one more time and the antibody was used as an antibody for biotin labeling.

(5) Labeling of antibody against carboxymethylated human serum albumin with biotin Biotin was labeled to the thus purified antibody using a Protein Biotinylation System kit (a product of Gibco Co., Ltd.).

To a solution prepared by diluting or concentrating the purified antibody against carboxymethylated human serum albumin with a 20 mM phosphate buffer solution (PH: 7.4) containing 0.15 M sodium chloride so as to have a concentration of 1.5 mg/ml was added a sodium carbonate buffer solution (PH: 9.0) so as to have a concentration of 0.05 M. Thereafter, to 6.7 ml of this antibody solution was added 26 μl of a CAB-NHS ester solution having a concentration of 50 mg/ml which was then stirred gently at room temperature for 1 hour. Ammonium chloride was further added to a concentration of 0.11 M to stop a reaction. Subsequently, the antibody solution was desalted in a column provided with this kit. Further, when the number of moles of the biotin introduced was calculated using Avidin/HABA attached to the kit, it was found that 14 moles of biotin were bound per 1 mole of the antibody against carboxymethylated human serum albumin.

(6) Antigen specificity of antibody against carboxymethylated human serum albumin The antigen specificity of the antibody against carboxymethylated human serum albumin was confirmed by a competitive ELISA method.

To the antibody solutions against carboxymethylated human serum albumin which was diluted with a 10 mM phosphate buffer solution (PH: 7.4) containing 0.15 M sodium chloride (to be abbreviated as PBS hereinafter) so as to each have a concentration of I pg/ml was added the prepared carboxymethylated human serum albumin so as to have concentrations of 0.1, 1, 10 and 100 μg/ml. Each of these solutions was left at 37° C. for 1 hour and used as an antibody solution inhibited by the carboxymethylated human serum albumin.

Carboxymethylated hemoglobin produced from hemoglobin (a product of Sigma Co., Ltd.) was prepared by the same method as that for the preparation of the carboxymethylated human serum albumin. The carboxymethylated hemoglobin was added to the antibody solutions against carboxymethylated human serum albumin having a concentration of 1 μg/ml so as to each have concentrations of 0.1, 1, 10 and 100 μg/ml. Each of these solutions were left at 37° C. for 1 hour and used as an antibody solution inhibited by the carboxymethylated hemoglobin.

Carboxymethylated β2M produced from β2 microglobulin (a product of Seikagaku Corporation) was prepared by the same method as that for the preparation of the carboxymethylated human serum albumin. The carboxymethylated β2M was added to the antibody solutions against carboxymethylated human serum albumin having a concentration of 1 μg/ml so as to each have concentrations of 0.1, 1, 10 and 100 μg/ml. Each of these solutions were left at 37° C. for 1 hour and used as an antibody solution inhibited by the carboxymethylated β2M.

Before a competitive ELISA method was carried out, the prepared carboxymethylated human serum albumin was diluted with PBS so as to have a concentration of 1 μg/ml. Thereafter, the diluted carboxymethylated human serum albumin solution was applied to a 96-well immunoplate (a product of NUNC Co.) in an amount of 100 μl per 1 well and left at 37° C. for 1 hour to immobilize the carboxymethylated human serum albumin on the immunoplate. After 1 hour, carboxymethylated human serum albumin which was not bound to the immunoplate was removed, and PBS containing 0.5% of gelatin was applied to the immunoplate in an amount of 100 μl per 1 well and left at 37° C. for 1 hour to block a portion of the immunoplate to which the carboxymethylated human serum albumin was not bound. After 1 hour, the gelatin solution was removed, the immunoplate was washed with PBS three times, and the antibody solutions inhibited by the carboxymethylated human serum albumin having each of the above concentrations or the antibody solutions inhibited by the carboxymethylated hemoglobin having each of the above concentrations or by the carboxymethylated 2M having each of the above concentrations was applied to the immunoplate in an amount of 100 μl per 1 well and left at 37° C. for 1 hour. Thereafter, the immunoplate was washed with PBS three times, and a solution of an anti-rabbit IgG antibody (a product of Cosmobio Co., Ltd) labeled with alkaline phosphatase having a concentration of 1 μg/ml was applied to the immunoplate in an amount of 100 μl per 1 well and left at 37° C. for 1 hour. Further, the immunoplate was washed with PBS three times, and a substrate solution prepared using an alkaline phosphatase substrate kit (a product of Bio-Rad Co., Ltd.) in accordance with the instruction manual attached to the kit was applied in an amount of 100 μl per 1 well. After it was left at room temperature for 5 minutes, 100 pi of a 0.4 M sodium hydroxide solution was added per 1 well to stop the reaction of alkaline phosphatase, and absorbance at 405 nm was measured. The results are shown in FIG. 1 and Table 1.

TABLE 1

Measurement results of antigen specificity of antibody against carboxymethylated human serum albumin

| Antigen | Concentration of inhibitor (μg/well) | Absorbance (A405) |
|---|---|---|
| human serum albumin | 0.01 | 0.93 |
|  | 0.1 | 0.997 |
|  | 1 | 1.004 |
|  | 10 | 1.052 |
| carboxymethylated human serum albumin | 0.01 | 0.656 |
|  | 0.1 | 0.267 |
|  | 1 | 0 |
|  | 10 | 0 |
| hemoglobin | 0.01 | 0.98 |
|  | 0.1 | 0.963 |
|  | 1 | 0.911 |
|  | 10 | 0.96 |
| carboxymethylated hemoglobin | 0.01 | 0.816 |
|  | 0.1 | 0.536 |
|  | 1 | 0.308 |
|  | 10 | 0.141 |
| β2 microglobulin | 0.01 | 0.91 |
|  | 0.1 | 0.9 |
|  | 1 | 0.92 |
|  | 10 | 0.9 |
| carboxymethylated β2 microglobulin | 0.01 | 0.703 |
|  | 0.1 | 0.387 |
|  | 1 | 0.194 |
|  | 10 | 0.066 |

It is suggested from the above results that the prepared antibody against carboxymethylated human serum albumin also exhibits reactivity with the carboxymethylated hemoglobin and the carboxymethylated β2M because an antigen-antibody reaction between the carboxymethylated human serum albumin and the antibody against carboxymethylated human serum albumin was inhibited not only by the carboxymethylated human serum albumin but also by the carboxymethylated hemoglobin and the carboxymethylated β2M.

(7) Measurement of carboxymethylated hemoglobin in blood of dialysis-related amyloidosis patients 50 μl of blood collected from each of 34 dialysis patients who had not: occurrence of diabetes mellitus but with dialysis-related amyloidosis by a vacuum blood-collecting tube containing EDTA-2K was washed with 250 μl of physiologic saline once and hypotonically lysed by addition of 1 ml of a diluted water to prepare a specimen.

Carboxymethylated hemoglobin contained in the specimen was measured by a dot blotting method. After the concentration of hemoglobin was measured by a cyanmethemoglobin method, the hemoglobin was adsorbed to a PVDF film (a product of Bio-Rad Co., Ltd.) in an amount of 500 ng using a dot blotting apparatus (a product of Bio-Rad Co., Ltd.). The film was immersed in a 20 mM phosphate buffer solution (PH: 7.4) containing 10% skimmed milk at room temperature for 1 hour and taken out, and 5 ml of the biotin labeled antibody solution against carboxymethylated human serum albumin having a concentration of 1 μg/ml was added. After 1 hour of incubation at room temperature, the film was washed with 50 ml of a 20 mM phosphate buffer solution (PH: 7.4) containing 0.05% of Tween 20 three times. Thereafter, to the film was added 5 ml of a biotin complex solution labeled with avidin-peroxytiase (Vectastine ABC Kit of Funakoshi K.K.) and incubation was carried out at room temperature for 1 hour. The film was washed with a 20 mM phosphate buffer solution containing 0.05% of Tween 20 (PH: 7.4) three times and 2 ml of an ECL western blotting detection reagent (a product of Amasham Co. Ltd) was added. The detection of luminescent intensity in the film was carried out using the Bio-Rad GS-363 Molecular Imager.

Figure 2:
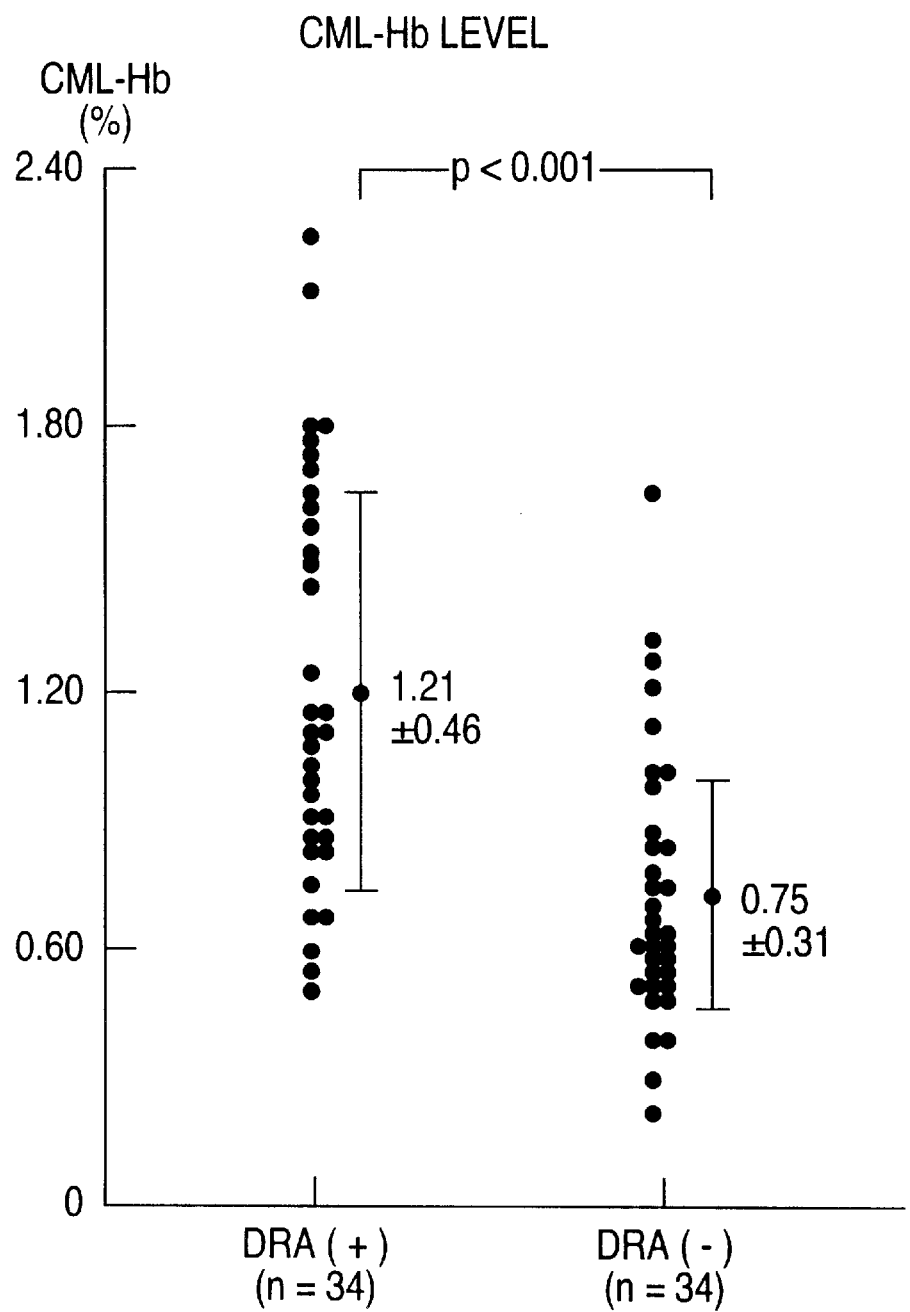
FIG. 2 is a graph showing the results of the difference of the carboxymethylation rate of hemoglobin between dialysis patients who have occurrence of amyloidosis and dialysis patients who have not occurrence of amyloidosis, in which the axis of ordinates shows the carboxymethylation rate of hemoglobin and the axis of abscissas shows the occurrence of dialysis-related amyloidosis.

As a control, carboxymethylated hemoglobin was measured by the same method as described above using the above prepared as a specimen (to obtain the carboxymethylation rate of hemoglobin derived from dialysis patients. The measurement results are shown in FIG. 2 as DRA (+). The average carboxymethylation rate of dialysis patients who had occurrence of dialysis-related amyloidosis was 1.21%.

COMPARATIVE EXAMPLE 1

The carboxymethylation rate of hemoglobin derived from a specimen was obtained in the same manner as in Example 1 except that the blood collected from each of 34 dialysis patients who had neither occurrence of diabetes mellitus nor dialysis-related amyloidosis was used as the specimen in place of the blood collected from dialysis patients who had occurrence of dialysis-related amyloidosis. The measurement results are shown in FIG. 2 as DRA (−). The average carboxymethylation rate of the dialysis patients who had not occurrence of dialysis-related amyloidosis was 0.75%.

The results show that the carboxymethylation rate of hemoglobin of dialysis patients who had occurrence of dialysis-related amyloidosis was much higher than that of dialysis patients who had not occurrence of dialysis-related amyloidosis. Therefore, it is understood that carboxymethylated hemoglobin is effectively useful as a marker for dialysis-related amyloidosis.

EXAMPLE 2

Figure 3:
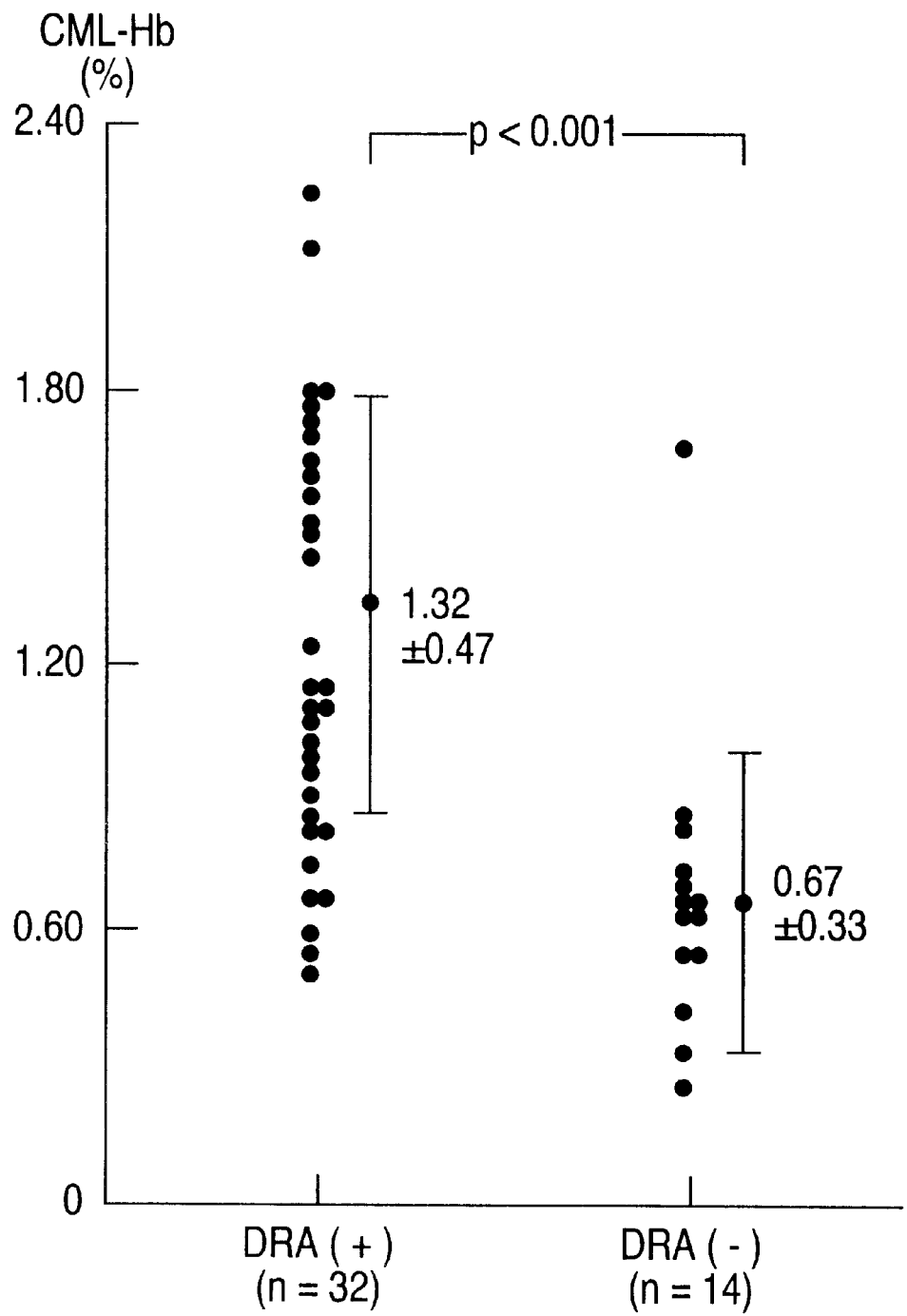
FIG. 3 is a graph showing the results of the difference of the carboxymethylation rate of hemoglobin between patients having dialysis for 100 months or more and having occurrence of amyloidosis and patients having dialysis for 100 months or more and having not occurrence of amyloidosis, in which the axis of ordinates shows the carboxymethylation rate of hemoglobin and the axis of abscissas shows the occurrence of dialysis-related amyloidosis.

Of dialysis patients who had occurrence of dialysis-related amyloidosis in Example 1, only patients who have had dialysis for 100 months or more were measured. The average carboxymethylation rate of hemoglobin of the patients was 1.32%. The results are shown in FIG. 3 as DRA (+).

COMPARATIVE EXAMPLE 2

Of dialysis patients who had not occurrence of dialysis-related amyloidosis in Comparative Example 1, only patients who have had dialysis for 100 months or more were measured. The average carboxymethylation rate of hemoglobin of the patients was 0.67%. The results are shown in FIG. 3 as DRA (−).

It is apparent from the results that there is a bigger difference of carboxymethylation rate between patients who have had dialysis for a long time and had occurrence of dialysis-related amyloidosis and patients who have had dialysis for a long time but had not occurrence of dialysis-related amyloidosis. Therefore, the carboxymethylated hemoglobin is more effectively useful as a marker for dialysis-related amyloidosis for patients who have had dialysis for a long time.

REFERENTIAL EXAMPLE 1

Figure 4:
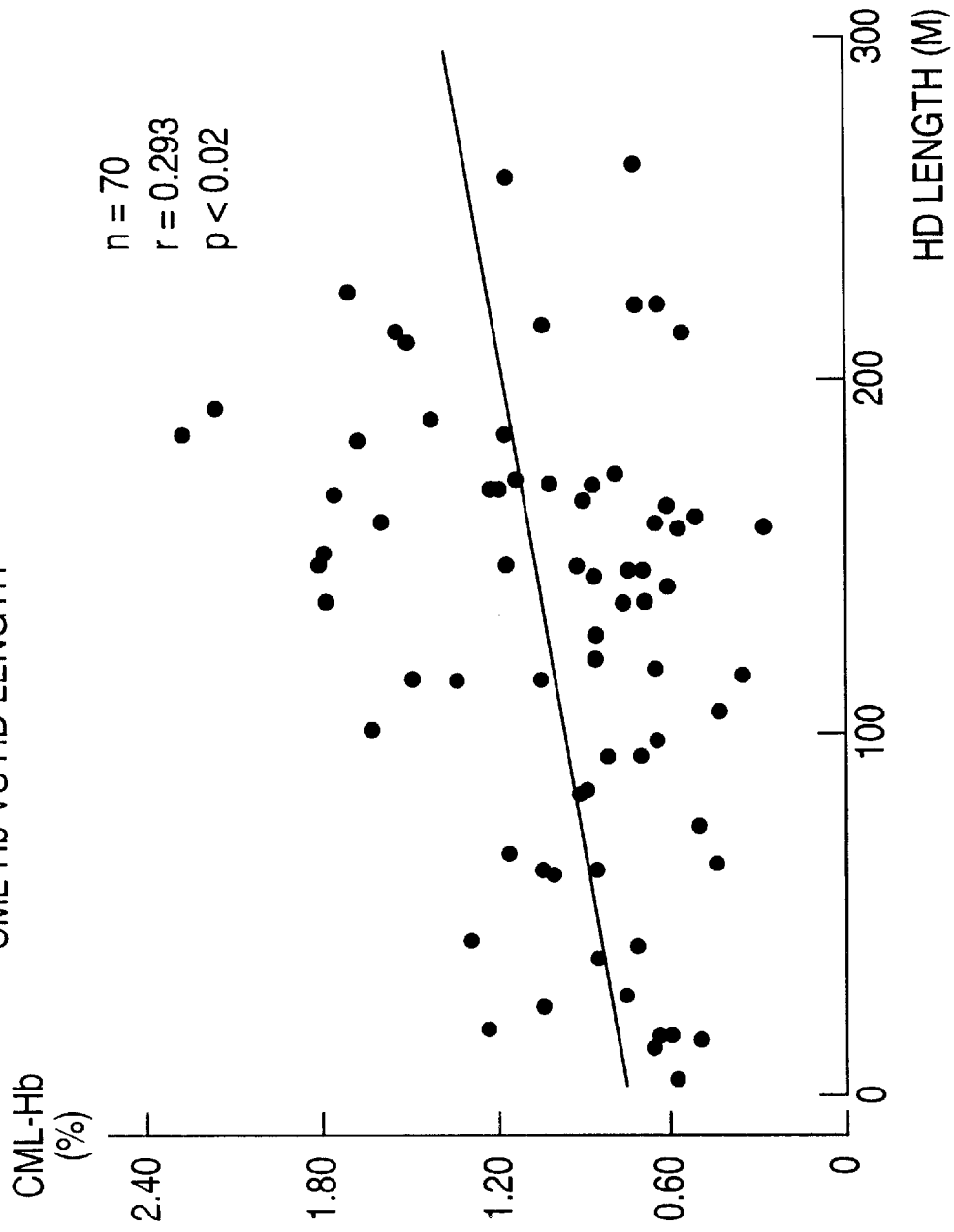
FIG. 4 is a graph showing the relationship between the dialysis period of each dialysis patient which is shown in the axis of abscissas and the carboxymethylation rate of hemoglobin which is shown in the axis ordinates.

The carboxymethylation rate of hemoglobin derived from a specimen was obtained in the same manner as in Example 1 except that the blood obtained from each of 70 patients who had dialysis regardless of the occurrence of dialysis-related amyloidosis was used as the specimen in place of dialysis patients who had occurrence of dialysis-related amyloidosis in Example 1. When the relationship between the period of dialysis of the patients and the measured carboxymethylation rate of hemoglobin was investigated, it was observed that the carboxymethylation rate tended to increase as the period of dialysis became longer. However, a strong correlation between these was not seen (correlation coefficient r=0.293). The results are shown in FIG. 4.

It is understood from Example 1, Comparative Example 1, Example 2, Comparative Example 2 and Referential Example 1 that an increase in the carboxymethylation rate of hemoglobin reflects the period of dialysis partially but mainly the presence of the occurrence of dialysis-related amyloidosis.

REFERENTIAL EXAMPLE 2

Figure 5:
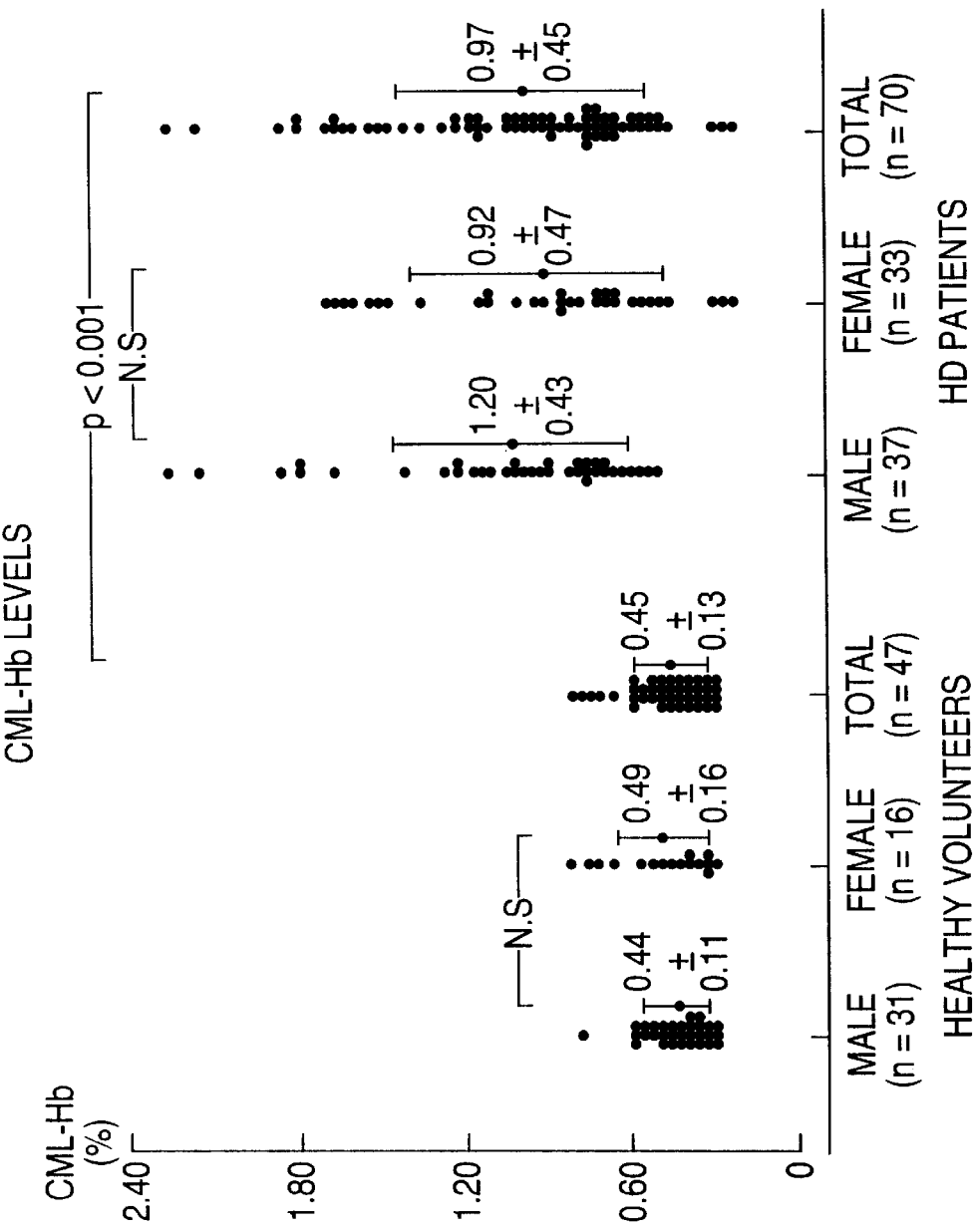
FIG. 5 is a graph showing the relationship between the sex and the carboxymethylation rate of hemoglobin of each dialysis patients or the sex and the carboxymethylation rate of hemoglobin of each healthy persons, in which the axis of ordinates shows the carboxymethylation rate of hemoglobin and the axis of abscissas shows the sex. This figure shows the relationship between the existence of a dialysis treatment which is shown in the axis of abscissas and the carboxymethylation rate of hemoglobin which is shown in the axis of ordinates.

When the carboxymethylation rate of male patients was compared with that of female patients, which were measured in Referential Example 1, the average carboxymethylation rate of male patients was 1.20% and that of female patients was 0.92%. Therefore, there is not so much difference between them. The results are shown in FIG. 5.

Therefore, it is apparent that the carboxymethylation rate of hemoglobin does not reflect the sex.

REFERENTIAL EXAMPLE 3

The carboxymethylation rate of hemoglobin derived from a specimen was obtained in the same manner as in Example 1 except that the blood obtained from each of 47 healthy people was used as the specimen in place of dialysis patients who had occurrence of dialysis-related amyloidosis. The measurement results are shown in FIG. 5. When the measured carboxymethylation rate of male patients was compared with that of female patients, the average carboxymethylation rate of male patients was 0.44% and that of female patients was 0.49%. Therefore, there was not so much difference between them. As a consequence, it has been made clear that the carboxymethylation rate of hemoglobin does not reflect the sex in the case of healthy people as well.

Further, when the carboxymethylation rate of dialysis patients obtained in Referential Example 1 was compared with the carboxymethylation rate of healthy people, the average carboxymethylation rate of dialysis patients was 0.97% and that of healthy people was 0.45%. Therefore, there was a big difference between them.

This suggests that the carboxymethylation rate of hemoglobin of a case of nephropathy is higher than that of a healthy person.

EXAMPLE 3

(1) Preparation of carboxymethylated peptide

To carboxymethylate the N-terminal amino groups of a synthetic peptide (valine-histidine-leucine-threonine-proline-glutamic acid-glutamic acid) SEQ ID NO: 1: Val His Leu Thr Pro Glu Glu having arrangement derived from the β-chain of hemoglobin, 1 ml of the synthetic peptide having a pH value of 9 and a concentration of 1 mg/ml was mixed with 1 ml of 0.25 M glyoxylic acid (a product of Sigma Co., Ltd) having a pH value of 9, and the mixture was left to stand at 0° C. for 12 hours. Thereafter, 1 mg of sodium cyanoborohydride was added to the resulting mixture and left to stand for another 12 hours.

As a control, a synthetic peptide was treated in the same manner as described above except that glyoxylic acid was not added.

The carboxymethylation rates of the above treated synthetic peptides were obtained by measuring unreacted amino groups using trinitrobenzenesulfonic acid (to be abbreviated as TNBS hereinafter:) in accordance with the following manner.

That is, 0.5 ml of each sample was added to 0.5 ml of a 0.1 M sodium hydroxide aqueous solution containing 0.1 M sodium tetraborate. Thereafter, 20 μl of 1.1 M TNBS recrystallized and washed with a diluted hydrochloric acid was added to the above solution, and then stirred. After 30 minutes, 2 ml of 98.5 mM sodium dihydrogen phosphate containing 1.5 mM sodium sulfide was added to terminate the reaction. When the absorbance at 420 nm was measured, the absorbance of carboxymethylated human serum albumin was found to be 0.03 and the absorbance of synthetic peptide (control) which was not treated with glyoxylic acid was found to be 1.25. When a system containing no synthetic peptide was measured in the same manner, the absorbance was 0.03. Therefore, it was found that the carboxymethylation rate of carboxymethylated synthetuc peptide was 100%.

(2) Coupling between carboxymethylated peptide and bovine serum albumin

The above prepared carboxymethylated peptide was coupled with bovine serum albumin (to be abbreviated as "BSA" hereinafter) using 1-ethyl-3-(3-dimethylaminopropy.l)carbodiimide hydrochloride (EDCI)(a product of Sigma Co., Ltd.) and N-hydroxysuccinic acid imide (a product of Wako Pure Chemical Industries, Ltd.). That is, after all the raw materials were cooled on ice, 228 µl of an N-hydroxysuccinic acid imide aqueous solution having a concentration of 10 mg/ml was added to, and mixed with, 500 µl of a carboxymethylated peptide aqueous solution having a concentration of 2.4 mg/ml. Thereafter, the mixture was added with 1.5 ml of an EDCI aqueous solution having a concentration of 20 mg/ml, stirred quickly and reacted on ice for 15 minutes. Then, 1,160 µl of a BSA aqueous solution having a concentration of 5 mg/ml was added thereto and left to stand at 4° C. for one night. Further, an uncoupled portion of the carboxymethylated peptide was removed by a dialysis membrane (a product of Wako Pure Chemical Industries, Ltd.) having a fractionated molecular weight of about 10,000. As a control, a synthetic peptide SEQ ID NO: 1: whose N-terminal was protected by a Boc group (Boc-valine-histidine-leucine-threonine-proline-glutamic acid-glutamic acid) was coupled with BSA in the same manner as described above so that the amount of the synthetic peptide became 10 times that of a conjugate of the carboxymethylated peptide and BSA.

(3) Preparation of antibody against carboxymethylated peptide

This was carried out entirely in the same manner as in Example 1.

(4) Preparation of affinity purification column 5 ml of Affi-gel 15 (a product of Bio-Rad Co., Ltd.) was washed with 15 ml of a 10 mM acetate buffer solution (PH: 4.5), and 11.6 ml of a conjugate solution containing the above Boc protected peptide and bovine serum albumin having a concentration of 5 mg/ml was added and stirred gently at room temperature for 1 hour. Thereafter, an unreacted portion of the conjugate of the Boc protected peptide and bovine serum albumin was removed by filtration, 30 ml of a 1 M ethanolamine solution was added and stirred gently at room temperature, and an unreacted portion of N-hydroxysucciimide ester was blocked. A carrier having immobilized the conjugate of the Boc protected peptide and bovine serum albumin was charged into a column and washed with ion exchange water until the absorbance thereof at 280 nm became 0. Further, the column was equilibrated with a 20 mM phosphate buffer solution (PH: 7.4) containing 0.15 M sodium chloride.

(5) Affinity purification of antibody against carboxymethylated peptide

This was carried out entirely in the same manner as in Example 1 except that a carboxymethylated peptide was used in place of carboxymethylated human serum albumin.

(6) Labeling of antibody against carboxymethylated peptide with biotin

This was carried out entirely in the same manner as in Example 1 except that a carboxymethylated peptide was used in place of carboxymethylated human serum albumin. 14 Moles of biotin were bound to 1 mole of the antibody against the carboxymethylated peptide.

(7) Antigen specificity of antibody against carboxymethylated human serum albumin The antigen specificity of the antibody against carboxymethylated peptide was confirmed by a competitive ELISA method.

To the antibody solutions against a carboxymethylated peptide which was diluted with a 10 mM phosphate buffer solution (PH: 7.4) containing 0.15 M sodium chloride (to be abbreviated as PBS hereinafter) so as to each have a concentration of 1 µg/ml was added the prepared conjugate of the carboxymethylated peptide and BSA (to be abbreviated as CM-BSA hereinafter) so as to have concentrations of 0.1, 1, 10 and 100 µg/ml. Each of these solutions was left at 37° C. for 1 hour and used as an antibody solution inhibited by CM-BSA.

Carboxymethylated hemoglobin produced from hemoglobin (a product of Sigma Co., Ltd.) was prepared by the same method as that for the preparation of the carboxymethylated peptide. The carboxymethylated hemoglobin was added to the antibody solutions against the carboxymethylated peptide having a concentration of 1 µg/ml so as to each have concentrations of 0.1, 1, 10 and 100 µg/ml. Each of these solutions were left at 37° C. for 1 hour and used as an antibody solution inhibited by the carboxymethylated hemoglobin.

Before a competitive ELISA method was carried out, the prepared CM-BSA was diluted with PBS so as to have a concentration of 1 µg/ml. Thereafter, the diluted CM-BSA solution was applied to a 96-well immunoplate (a product of NUNC Co., Ltd) in an amount of 100 µl per 1 well and left at 37° C. for 1 hour to immobilize the CM-BSA on the immunoplate. After 1 hour, CM-BSA which was not bound to the immunoplate was removed, and PBS, containing 0.5% of gelatin was applied to the immunoplate in an amount of 100 µl per 1 well and left at 37° C. for 1 hour to block a portion of the immunoplate to which the CM-BSA was not bound. After 1 hour, the gelatin solution was removed, the immunoplate was washed with PBS three times, and the antibody solutions inhibited by the CM-BSA having each of the above concentrations or the antibody solutions inhibited by the carboxymethylated hemoglobin having each of the above concentrations was applied to the immunoplate in an amount of 100 µl per 1 well and left at 37° C. for 1 hour. Thereafter, the immunoplate was washed with PBS three times, and a solution of an anti-rabbit IgG antibody (a product of Cosmobio Co., Ltd) labeled with alkaline phosphatase having a concentration of 1 µg/ml was applied in an amount of 100 µl per 1 well and left at 37° C. for 1 hour. Further, the immunoplate was washed with PBS three times, and a substrate solution prepared using an alkaline phosphatase substrate kit (a product of Bio-Rad Co., Ltd.) in accordance with the instruction manual attached to the kit was applied in an amount of 100 µl per 1 well. After it was left at room temperature for 5 minutes, 100 µl of a 0.4 M sodium hydroxide solution was added per 1 well to stop the reaction of alkaline phosphatase and absorbance at 405 nm was measured. It is suggested from the results that the prepared antibody against the carboxymethylated peptide exhibits reactivity not only with a carboxymethylated peptide but also with carboxymethylated hemoglobin because an antigen-antibody reaction between CM-BSA and the antibody against the carboxymethylated peptide was also inhibited by the carboxymethylated hemoglobin.

(8) Measurement of carboxymethylated hemoglobin in blood derived from case of diabetes mellitus 50 µl of blood collected from each of 8 cases of diabetes mellitus who did not suffer from complications by a vacuum blood-collecting tube containing EDTA-2K was washed with 250 µl of physiologic saline once and hypotonically lysed by addition of 1 ml of a distilled water to prepare a specimen. The average age of the cases was 62.1.

Carboxymethylated hemoglobin contained in the specimen was measured by a dot blotting method. After the concentration of hemoglobin was measured by a cyanmethemoglobin method, the hemoglobin was adsorbed to a PVDF film (a product of Bio-Rad Co., Ltd.) in an amount of 500 ng using a dot blotting apparatus (a product of Bio-Rad Co., Ltd.). The film was immersed in a 20 mM phosphate buffer solution (PH: 7.4) containing 10% skimmed milk at room temperature for 1 hour and taken out, and 5 ml of the biotin-labeled antibody solution against carboxymethylated peptide having a concentration of 1 µg/ml was added. After 1 hour of incubation at room temperature, the film was washed with 50 ml of a 20 mM phosphate buffer solution (PH: 7.4) containing 0.05% of Tween 20 three times. Thereafter, to the film was added 5 ml of a biotin complex solution labeled with avidin-peroxydase (Vectastine ABC Kit of Funakoshi K. K.) and incubation was carried out at room temperature for 1 hour. The film was washed with a 20 mM phosphate buffer solution (PH: 7.4) containing 0.05% of Tween 20 three times and 2 ml of an ECL western blotting detection reagent (a product of Amasham Co., Ltd) was added. The detection of luminescent intensity in the film was carried out using the Bio-Rad GS-363 Molecular Imager.

As a control, carboxymethylated hemoglobin was measured by the same method as described above using commercial hemoglobin (a product of Sigma Co., Ltd.) as a specimen. The luminescent intensity of hemoglobin derived from the above cases of diabetes mellitus is shown below when the luminescent intensity of the commercial hemoglobin is 100. The measured values of luminescent intensity are also shown below. The measurement results are shown in Table 2.

TABLE 2

Measurement results of carboxymethylated hemoglobin contained in blood derived from cases of diabetes mellitus

| Specimen No. | Luminescent intensity (relative value) | Luminescent intensity (measured value) |
|---|---|---|
| 1 | 338 | 1609 |
| 2 | 362 | 1723 |
| 3 | 378 | 1799 |
| 4 | 302 | 1437 |
| 5 | 240 | 1143 |
| 6 | 419 | 1994 |
| 7 | 283 | 1347 |
| 8 | 522 | 2485 |
| control 1) | 100 | 476 |

Note 1) The specimen is commercial hemoglobin.

EXAMPLE 4

Carboxymethylated hemoglobin contained in a specimen was measured in accordance with the method of Example 3 except blood collected from each of 7 cases of diabetes mellitus complications who suffered from nephropathy or retinopathy in addition to diabetes mellitus was used as the specimen in place of blood derived from the cases of diabetes mellitus. The average age of the cases was 66.3. The measurement results are shown in Table 3.

TABLE 3

Measurement results of carboxymethylated hemoglobin contained in blood derived from cases of diabetes mellitus complications

| Specimen No. | Luminescent intensity (relative value) | Luminescent intensity (measured value) |
|---|---|---|
| 1 | 495 | 2356 |
| 2 | 620 | 2951 |
| 3 | 519 | 2470 |
| 4 | 637 | 3032 |
| 5 | 472 | 2247 |
| 6 | 449 | 2137 |
| 7 | 841 | 4003 |
| control 1) | 100 | 476 |

Note 1) The specimen is commercial hemoglobin

COMPARATIVE EXAMPLE 3

Carboxymethylated hemoglobin contained in a specimen was measured in accordance with the method of Example 3 except blood collected from each of 10 healthy people was used as the specimen in place of blood derived from the cases of diabetes mellitus. The average age of the healthy people was 60.5. The measurement results are shown in Table 4.

When the luminescent intensities of the group of cases of diabetes mellitus measured in Example 3 were compared with those of healthy persons statistically (t-test), the luminescent intensities of the group of the cases of diabetes mellitus were much higher than those of the healthy persons with a significant difference (p,0.05%). This means that blood derived from a case of diabetes mellitus contains much more hemoglobin having carboxymethylated N-terminals than blood derived from a healthy person.

When the luminescent intensities of cases of diabetes mellitus complications measured in Example 4 were compared with those of healthy persons by t-test, the luminescent intensities of the group of cases of diabetes mellitus complications were much higher than those of the healthy persons with a significant difference (p,0.05%). This means that blood derived from a case of diabetes mellitus complications contains much more hemoglobin having carboxymethylated N-terminals than blood derived from a healthy person.

TABLE 4

Measurement results of carboxymethylated hemoglobin contained in blood derived from healthy person

| Specimen No. | Luminescent intensity (relative value) | Luminescent intensity (measured value) |
|---|---|---|
| 1 | 129 | 614 |
| 2 | 143 | 681 |

TABLE 4-continued

Measurement results of carboxymethylated hemoglobin
contained in blood derived from healthy person

| Specimen No. | Luminescent intensity (relative value) | Luminescent intensity (measured value) |
|---|---|---|
| 3 | 151 | 719 |
| 4 | 207 | 985 |
| 5 | 125 | 595 |
| 6 | 145 | 690 |
| 7 | 105 | 500 |
| 8 | 95 | 452 |
| 9 | 98 | 467 |
| 10 | 133 | 633 |
| control 1) | 100 | 476 |

Note 1) The specimen is commercial hemoglobin

What is claimed is:

1. A method for diagnosing or evaluating dialysis-related amyloidosis in a dialysis patient comprising:

obtaining a sample of blood from the patient and lysing at least a portion of blood cells from the sample to provide a specimen of hemoglobin;

reacting the hemoglobin specimen with an isolated antibody specific for an epitope comprising a carboxymethylated amino acid residue under conditions sufficient for antibody binding to any of said epitope present in hemoglobin in the specimen;

detecting a level of binding of the antibody to the hemoglobin wherein the binding level is indicative of carboxymethylated hemoglobin level in the specimen and said carboxymethylated hemoglobin level is used in diagnosing or evaluating dialysis-related amyloidosis in the dialysis patient.

2. The method of claim 1, wherein the epitope comprises an amino acid sequence of hemoglobin and said carboxymethylated amino acid residue is an amino acid having a side-chain amino group which is carboxymethylated.

3. A method for diagnosing or evaluating diabetes mellitus or diabetes mellitus complications in a patient comprising:

obtaining a sample of blood from the patient and lysing at least a portion of blood cells from the sample to provide a specimen of hemoglobin;

reacting the hemoglobin specimen with an isolated antibody specific for an epitope comprising a $N^\alpha$-carboxymethylated amino acid residue of hemoglobin under conditions sufficient for antibody binding to any of said epitope present in hemoglobin in the specimen;

detecting a level of binding of the antibody to the hemoglobin wherein the binding level is indicative of $N^\alpha$-carboxymethylated hemoglobin level in the specimen and said $N^\alpha$-carboxymethylated hemoglobin level is used in diagnosing or evaluating diabetes mellitus or diabetes mellitus complication in the patient.

4. An isolated antibody which reacts specifically with a N-terminal epitope of carboxymethylated hemoglobin in which the N-terminal amino acid of the epitope is $N^\alpha$-carboxymethylated.

5. An immuno logical reagent for the diagnosis or evaluation of diabetes mellitus or of diabetes mellitus complications or treatments comprising the antibody of claim 4.

6. An immunological reagent for the diagnosis or evaluation of the effect of a medical for the treatment of diabetes mellitus complications, comprising the antibody of claim 4.

* * * * *